United States Patent
Ishii et al.

(10) Patent No.: US 6,942,878 B2
(45) Date of Patent: Sep. 13, 2005

(54) COSMETIC COMPOSITION

(75) Inventors: Nobuaki Ishii, Kawasaki (JP); Kouichi Wada, Kawasaki (JP); Junko Futami, Yokohama (JP); Michihiro Takama, Kawasaki (JP)

(73) Assignee: Showa Denko K.K., Tokyo (JP)

( * ) Notice: Subject to any disclaimer, the term of this patent is extended or adjusted under 35 U.S.C. 154(b) by 92 days.

(21) Appl. No.: 10/363,664

(22) PCT Filed: Sep. 10, 2001

(86) PCT No.: PCT/JP01/07825

§ 371 (c)(1),
(2), (4) Date: Mar. 5, 2003

(87) PCT Pub. No.: WO02/22098

PCT Pub. Date: Mar. 21, 2002

(65) Prior Publication Data

US 2003/0180232 A1 Sep. 25, 2003

Related U.S. Application Data

(60) Provisional application No. 60/275,466, filed on Mar. 14, 2001.

(30) Foreign Application Priority Data

Sep. 11, 2000 (JP) ..................................... 2000-274463

(51) Int. Cl.[7] ............................................... A61K 9/14
(52) U.S. Cl. ...................... 424/489; 424/490; 424/59; 424/600; 424/641; 424/642; 424/682
(58) Field of Search .................... 424/401, 489, 424/490, 59, 600, 641, 642, 682

(56) References Cited

U.S. PATENT DOCUMENTS

| 4,927,464 A | 5/1990 | Cowie |
| 5,032,390 A | * 7/1991 | Iwaya et al. .................. 424/59 |

FOREIGN PATENT DOCUMENTS

| EP | 0 433 086 A | 6/1991 |
| EP | 0 599 492 A | 6/1994 |
| EP | 0 688 834 A | 12/1995 |
| EP | 0 748 624 A | 12/1996 |
| EP | 0 824 086 A | 2/1998 |
| WO | WO 96 28137 A | 9/1996 |

* cited by examiner

Primary Examiner—Shelley A. Dodson
Assistant Examiner—Konata M. George
(74) Attorney, Agent, or Firm—Sughrue Mion, PLLC

(57) ABSTRACT

To provide a cosmetic composition having excellent ultraviolet protection against both UVB and UVA, causing neither unpleasant whitening to the applied skin nor skin irritation, and ensuring good feeling on use and high safety and high stability without causing decomposition of the ingredients blended in the cosmetic material, such as organic ultraviolet absorber. A cosmetic composition obtained by using fine particulate titanium oxide and fine particulate zinc oxide each surface-treated with silica, alumina or alumina/silica and having a primary particle size of 0.01 to 0.2 μm in combination and blending titanium oxide and zinc oxide at a mass ratio of 1:4 to 2:3, wherein SPF is maintained as compared with the case where the mass ratio of titanium oxide to zinc oxide is 1:0, and when applied to a thickness of 10 μm, the whiteness W value measured using the CIE color specification system is 20 or less.

22 Claims, 1 Drawing Sheet

LIGHT TRANSMITTANCE OF SILICA-COATED PRODUCT

COSMETIC COMPOSITION

CROSS-REFERENCE TO RELATED APPLICATIONS

This application claims the benefit pursuant to 35 U.S.C. §119(e)(1) of U.S. Provisional Application, No. 60/275,466 filed on Mar. 14, 2001, pursuant to 35 U.S.C. §111(b).

TECHNICAL FIELD

The present invention relates to a cosmetic composition, particularly a cosmetic composition having a capability of ultraviolet protection. More specifically, the present invention relates to a cosmetic composition capable of providing excellent ultraviolet protection against both ultraviolet B (UVB; radiation having a wavelength of 290 to 320 nm) and ultraviolet A (UVA; radiation having a wavelength of 320 to 400 nm), causing neither unpleasant whitening to the applied skin nor skin irritation, and ensuring good feeling on use and high safety and high stability without causing decomposition of the ingredients blended in the cosmetic material, such as organic ultraviolet absorber.

BACKGROUND ART

Conventionally, an organic compound-based ultraviolet absorber, an inorganic compound-based ultraviolet-shielding agent or the like is blended in cosmetic compositions having a capability of ultraviolet protection. The organic compound-based ultraviolet absorber now on use includes 2-ethylhexyl p-methoxycinnamate for UVB protection and 4-tert-butyl-4'-methoxydibenzoylmethane for UVA protection. However, when these are blended in a large amount so as to enhance the capability of ultraviolet protection, a problem of increase in stickiness or skin irritation arises. Furthermore, 4-tert-butyl-4'-methoxydibenzoylmethane and the like cannot be stably blended because of their low solubility in an oil agent and coloration due to chelation with metal ion. In addition, these UV absorbers are poor in the photostability and their decomposition jeopardize the safety.

On the other hand, with increasing attention to the safety of cosmetics, use of an inorganic compound-based ultraviolet-shielding agent is widespread and in particular, titanium oxide and zinc oxide are used for general purposes. However, if titanium oxide is blended in a high proportion so as to obtain sufficiently high protection against ultraviolet rays, dry or powdery feeling is generated and when applied to skin, unpleasant whitening seriously occurs. As compared with titanium oxide, zinc oxide is low in the capability of ultraviolet protection per unit mass despite its excellent transparency and therefore, for obtaining sufficiently high ultraviolet protection, zinc oxide must be blended in a higher proportion than titanium oxide, as a result, dry or powdery feeling is generated and moreover, aggregation/gelling takes place due to the elution of zinc ion.

These inorganic compound-based ultraviolet-shielding agents have photocatalytic activity and therefore, are surface-treated with silica, alumina or the like, however, the concealing effect is insufficient and other cosmetic base materials including an organic compound-based ultraviolet absorber are decomposed.

As such, the kind and the blending amount of the ultraviolet-protecting agent which can be blended in cosmetic compositions for preventing sunburn are limited and a fully satisfactory ultraviolet-protecting agent has not been found.

DISCLOSURE OF INVENTION

On of the objects of the present invention is to provide a cosmetic composition having high capability of ultraviolet protection against UVB and UVA, causing neither unpleasant whitening to the applied skin nor skin irritation, ensuring good feeling on use. One of the objects of the present invention is to provide a cosmetic composition having high safety and stability while preventing the decomposition of ingredients blended in cosmetics, such as organic ultraviolet absorber.

As a result of extensive investigations to attain the above-described objects, the present inventors have found that the sole use of titanium oxide gives a sufficiently high SPF but cannot be satisfied in preventing the unpleasant whitening and the sole use of zinc oxide can give neither sufficiently high SPF nor UVB protection effect, nevertheless, when particulate titanium oxide and particulate zinc oxide each coated with a certain dense silica film and having a primary particle size of 0.01 to 0.2 μm are used in combination and blended at a mass ratio of particulate titanium oxide to particulate zinc oxide of 1:4 to 2:3, the obtained cosmetic composition can be synergistically elevated in the ultraviolet protection effect, maintain the same high SPF of 30 or more as in the sole use of titanium oxide, be free of generation of the unpleasant whitening on the applied skin, be extremely reduced in the skin irritation and ensure excellent feeling on use and high safety and stability while preventing the decomposition of ingredients blended in cosmetics, such as organic ultraviolet absorber. The present invention has been accomplished based on this finding.

More specifically, the present invention relates to the following matters.

[1] A cosmetic composition having blended therein silica-, alumina- or alumina/silica-coated particulate titanium oxide and silica-, alumina- or alumina/silica-coated particulate zinc oxide at a mass ratio of 1:4 to 2:3, the particulate titanium oxide and the particulate zinc oxide each having an average primary particle size of 0.01 to 0.2 μm.

[2] The cosmetic composition as described in [1] above, which comprises the silica-, alumina- or alumina/silica-coated particulate titanium oxide and the silica-, alumina- or alumina/silica-coated particulate zinc oxide in total amount of 5 to 25% by mass based on the amount of the cosmetic composition.

[3] The cosmetic composition as described in [1] or [2] above, which comprises an organic ultraviolet absorber.

[4] The cosmetic composition as described in [1] or [2] above, which comprises from 2 to 8% by mass of 2-ethylhexyl p-methoxycinnamate.

[5] The cosmetic composition as described in [1] or [2] above, which comprises from 0.1 to 3% by mass of 4-tert-butyl-4'-methoxydibenzoylmethane.

[6] The cosmetic composition as described in any one of [1] to [5] above, wherein the cosmetic composition maintains the same SPF (Sun Protection Factor) value as in the sole use of titanium oxide and when the cosmetic composition is applied to a thickness of 10 μm, the whiteness W value measured using the CIE (International Commission on Illumination) color specification system is 20 or less.

[7] The cosmetic composition as described in [6] above, wherein the SPF (Sun Protection Factor) value is 30 or more.

[8] The cosmetic composition as described in any one of [1] to [7] above, wherein the PFA (Protection Factor of UVA) of the cosmetic composition is 4 or more.

[9] The cosmetic composition as described in any one of [6] to [8] above, wherein the W value is 15 or less.

[10] The cosmetic composition as described in any one of [1] to [9] above, wherein the particulate titanium oxide and the particulate zinc oxide each is coated with silica and the silica film has a thickness of 0.1 to 100 nm.

[11] The cosmetic composition as described in [10] above, wherein the surfaces of the silica-coated particulate titanium oxide and zinc oxide are further made hydrophobic by using a hydrophobizing agent.

[12] The cosmetic composition as described in [11] above, wherein the hydrophobizing agent is one or more selected from the group consisting of silicone oils, alkoxysilanes, silane coupling agents, and higher fatty acid salts.

[13] The cosmetic composition as described in any one of [10] to [12] above, wherein the silica-coated particulate titanium oxide and the silica-coated particulate zinc oxide each has a photocatalytic activity, determined by a tetralin auto-oxidation method, of 60 Pa/min or less.

[14] The cosmetic composition as described in any one of [10] to [13] above, wherein the silica-coated particulate titanium oxide and the silica-coated particulate zinc oxide each has a dye discoloration rate ($\Delta ABS_{490}$/hr), determined by a Sunset Yellow method, of 0.1 or less.

[15] The cosmetic composition as described in any one of [10] to [14] above, wherein the silica-coated particulate titanium oxide and the silica-coated particulate zinc oxide each has an organic ultraviolet absorber decomposition rate ($\Delta ABS_{340}$/hr), determined by a Parsol 1789 method, of 0.02 or less.

[16] The cosmetic composition as described in any one of [10] to [15] above, wherein the silica-coated particulate titanium oxide and the silica-coated particulate zinc oxide each has an organic ultraviolet absorber decomposition percentage, determined by an ethylhexyl p-methoxycinnamate method, of 5% or less.

[17] The cosmetic composition as described in any one of [10] to [16] above, wherein the silica-coated particulate titanium oxide and the silica-coated particulate zinc oxide each has a kinetic friction coefficient, determined by a glass plate method, of 0.550 or less.

[18] A method for producing a cosmetic composition, comprising bringing particulate titanium oxide and particulate zinc oxide each having an average primary particle size of 0.01 to 0.2 μm as a mixture (at a mass ratio of 1:4 to 2:3) or separately into contact with a silica film-forming composition containing water, an alkali, an organic solvent and a silicic acid having neither an organic group nor a halogen or a precursor capable of producing the silicic acid, with the water/organic solvent ratio being from 0.1 to 10 and the silicic acid concentration being from 0.0001 to 5 mol/liter, thereby coating the particulate titanium oxide and the particulate zinc oxide with silica, and drying and blending these particles.

[19] The method for producing a cosmetic composition as described in [18] above, which comprises blending from 2 to 8% by mass of 2-ethylhexyl p-methoxycinnamate.

[20] The method for producing a cosmetic composition as described in [18] above, which comprises blending from 0.1 to 3% by mass of 4-tert-butyl-4'-methoxydibenzoylmethane.

[21] An ultraviolet-protecting cosmetic material comprising the cosmetic composition described in any one of [1] to [17] above.

[22] The ultraviolet-protecting cosmetic material as described in [21] above, which is a W/O or O/W milky lotion, a cream, a foundation or a jell.

In the present invention, "silica-, alumina- or alumina/silica-coated particulate titanium oxide and silica-, alumina- or alumina/silica-coated particulate zinc oxide" include the following:

(i) Particulate titanium oxide coated with silica and particulate zinc oxide coated with silica.

(ii) Particulate titanium oxide coated with silica and particulate zinc oxide coated with alumina.

(iii) Particulate titanium oxide coated with silica and particulate zinc oxide coated with a mixture of alumina and silica.

(iv) Particulate titanium oxide coated with alumina and particulate zinc oxide coated with silica.

(v) Particulate titanium oxide coated with alumina and particulate zinc oxide coated with alumina.

(vi) Particulate titanium oxide coated with alumina and particulate zinc oxide coated with a mixture of alumina and silica.

(vii) Particulate titanium oxide coated with a mixture of alumina and silica and particulate zinc oxide coated with silica.

(viii) Particulate titanium oxide coated with a mixture of alumina and silica and particulate zinc oxide coated with alumina.

(ix) Particulate titanium oxide coated with a mixture of alumina and silica and particulate zinc oxide coated with a mixture of alumina and silica.

BEST MODE FOR CARRYING OUT THE INVENTION

The mode for carrying out the invention is described in detail below, however, the present invention is not limited thereto.

SPF is an abbreviation of Sun Protection Factor and this is a value measured under test conditions according to the standards of SPF measuring method (JCIA method) provided on January, 1992 by Japan Cosmetic Industry Association (JCIA). This value (sun protection factor) indicates an effect of preventing sunburn (i.e., erythema primarily resultant from sunburn by UVB).

The SPF is determined by the following formula (I):

$$SPF = \frac{\text{minimum erythema dose} (MED) \text{ of skin applied with sunscreen}}{\text{minimum erythema dose} (MED) \text{ of unapplied skin}} \quad (I)$$

Theoretically, a sunscreen having an SPF of 30 is known to have a sufficiently high effect of UVB ultraviolet protection and even when an average type of person applied with the sunscreen to an amount (2 mg/cm$^2$) prescribed by the JCIA method basks in the sun all day, sunburn does not occur. However, the SPF is preferably 40 or more.

PA is an abbreviation of Protection Grade of UVA and this is a value measured under test conditions according to the standards of UVA protection effect measuring method provided on January, 1996 by Japan Cosmetic Industry Association. This value (UVA protection factor) indicates a persistent pigment darkening (primarily caused by UVA) protection. It is defined that PFA of 2 to less than 4 is "PA+", PFA of 4 to less than 8 is "PA++", and PFA of 8 or more is "PA+++".

PFA is determined by the following formula (II):

$$PFA = \frac{\text{Minimum persistent pigment darkening dose}}{\text{minimum persistent pigment darkening}} \quad \text{(II)}$$
$$\text{(MPPD) of skin applied with sunscreen}$$
$$\text{dose (MPPD) of unapplied skin}$$

Theoretically, a sunscreen having a PFA of "PA++" is known to have a sufficiently high effect of UVA ultraviolet protection and even when an average type of person applied with the sunscreen to an amount (2 mg/cm$^2$) prescribed by JCIA basks in the sun all day, persistent pigment darkening does not occur. However, the PFA is preferably PA+++ or more.

The W value is a whiteness degree measured using the XYZ color specification system provided by the CIE (International Commission on Illumination). In the present invention, the W value used is calculated by the following formula (III):

$$W=0.847Z \quad \text{(III)}$$

As the W value is larger, the whiteness is higher, that is, when a sunscreen is applied to skin, the unpleasant whiteness is more serious.

In the present invention, particulate titanium oxide and particulate zinc oxide are used at a specific mass ratio, whereby the obtained ultraviolet-protecting cosmetic composition can maintain the same capability of ultraviolet protection as in the sole use of particulate titanium oxide, can have a W value of 20 or less and high transparency and can ensure good feeling on use and high stability.

According to the present invention, the mass ratio of particulate titanium oxide to particulate zinc oxide is 1:4 to 2:3, preferably 1:3 to 2:3.

If the amount of titanium oxide as expressed by the mass ratio of particulate titanium oxide to particulate zinc oxide exceeds 2:3, unpleasant whiteness is intensified due to titanium oxide, whereas if the amount of titanium oxide as expressed by the mass ratio of particulate titanium oxide to particulate zinc oxide is less than 1:4, the ultraviolet protection may disadvantageously decrease despite good transparency at the time of application.

In the present invention, the term "maintain the same capability of ultraviolet protection" means a range including a variation of about 5%, for example, a range from 40 to 44 for the SPF value of 42 and a range from 7.5 to 8.5 for the PFA value of 8.

In the present invention, when the cosmetic composition of the present invention is applied to a thickness of 10 µm, the whiteness degree W value measured using the CIE color specification system is 20 or less, preferably 15 or less. If the W value exceeds 20, this means that when the cosmetic composition is actually applied to skin, unpleasant whitening is generated, for example, with an applied amount prescribed in the JCIA method (2 mg/cm$^2$).

The coated particulate titanium oxide and coated particulate zinc oxide, which are coated with silica, alumina or silica/alumina, are described below. In the present invention, silica coating is preferred.

The cosmetic composition of the present invention can use silica-coated particulate titanium oxide and silica-coated particulate zinc oxide which are obtained by a method of bringing particulate titanium oxide and particulate zinc oxide (at a mass ratio of 1:4 to 2:3) each having an average primary particle size of 0.01 to 0.2 µm into contact with a silica film-forming composition comprising water, an alkali, an organic solvent and a silicic acid having neither an organic group nor a halogen or a precursor capable of producing the silicic acid, with the water/organic solvent ratio by volume being from 0.1 to 10 and the silicon concentration being 0.0001 to 5 mol/liter, to selectively coat the surface of particulate titanium oxide or particulate zinc oxide with dense silica.

In this case, after the particulate titanium oxide and the particulate zinc oxide powder at a ratio described above are each independently contacted with the silica film-forming composition to perform the coating with silica, the obtained silica-coated particulate titanium oxide and the silica-coated particulate zinc oxide may be blended at a mass ratio of 1:4 to 2:3.

The silica-coated titanium oxide or silica-coated zinc oxide which can be more suitably used in the cosmetic composition of the present invention is coated with a dense silica film such that the ratio I of the absorption peak intensity at 1,150 to 1,250 cm$^{-1}$ to the absorption peak intensity at 1,000 to 1,100 cm$^{-1}$ on the infrared absorption spectrum (I=$I_1/I_2$, wherein $I_1$ is an absorption peak intensity at 1,150 to 1,250 cm$^{-1}$ and $I_2$ is an absorption peak intensity at 1,000 to 1,100 cm$^{-1}$) is 0.2 or more and the refractive index is 1.435 or more.

In the present invention, the silicic acid for use in the silica film-forming composition is an orthosilicic acid or a polymer thereof, such as metasilicic acid, mesosilicic acid, mesotrisilicic acid and mesotetrasilicic acid, described, for example, in the paragraph "Silicic Acid" of *Encyclopaedia Chimica*, 7th imp., Kyoritsu Shuppan (Mar. 15, 1969). The silicic acid does not contain an organic group or a halogen.

The composition containing a silicic acid can be obtained by adding water, an alkali and an organic solvent, for example, to tetraalkoxysilane (Si(OR)$_4$, wherein R is a hydrocarbon group, preferably an aliphatic group of $C_1$ to $C_6$), specifically a precursor such as tetramethoxysilane, tetraethoxysilane, tetra-n-propoxysilane, tetraisopropoxy silane and tetra-n-butoxy silane, stirring the mixture and thereby allowing a hydrolysis reaction to proceed.

This method is practical and preferred because of easiness in handling or operation. Among those materials, tetraethoxysilane is preferred.

A compound having a hydrophobic group such as hydrocarbon group, a halogen or a hydrogen, represented by the formula $X_n Si(OH)_{4-n}$ (wherein X is a hydrocarbon group, a halogen or a hydrogen and n is an integer of 1, 2 or 3) is different from the silicic acid for use in the present invention, accordingly, trialkoxyalkylsilane, dialkoxyalkyldialkylsilane, trialkoxysilane, dialkoxysilane and the like are not suitable as the precursor.

The composition containing a silicic acid can also be obtained by a method of hydrolyzing silane tetrahalogenide while adding thereto water, an alkali and an organic solvent, a method of adding an alkali and an organic solvent to water glass, or a method of treating water glass with a cationic exchange resin and adding thereto an alkali and an organic solvent. Tetraalkoxysilane, silane tetrahalogenide and water glass used as the starting material of silicic acid are not particularly limited and those widely and commonly used in industry or as a reagent may be used, however, a higher purity material is suitable. The silica film-forming composition for use in the present invention may contain an unreacted product of the above-described starting material for silicic acid.

The amount of silicic acid is not particularly limited but is preferably from 0.0001 to 5.0 mol/liter, more preferably from 0.001 to 5 mol/liter, in terms of the silicon concentration. If the silicon concentration is less than 0.0001 mol/liter, the silica film is formed at a very low rate and this is not practical, whereas if the silicon concentration exceeds 5 mol/liter, silica particles may be produced in the composition without forming a coating and this is not preferred.

The silicon concentration may be calculated from the amount of, for example, tetraalkoxysilane added but can also be measured by the atomic absorption spectrochemical analysis of the composition. The measurement may be performed using a spectrum of silicon at a wavelength of 251.6 nm for the analytical line and acetylene/nitrous oxide for the frame.

The water used for the silica film-forming composition is not particularly limited but water from which particles are removed by filtration or the like is preferably used, because if the water contains particles, the particles may be disadvantageously mixed into the product as an impurity.

The water for use in the silica film-forming composition is preferably used in an amount of giving a water/organic solvent ratio of 0.1 to 10 in terms of the volume ratio. If the water/organic solvent ratio by volume departs from this range, the film formation may fail or the film formation rate may extremely decreases. The water/organic solvent ratio by volume is more preferably from 0.1 to 0.5. Insofar as the water/organic solvent ratio by volume is from 0.1 to 0.5, the kind of alkali used is not limited. In the case where the water/organic solvent ratio by volume is 0.5 or more, the coating is preferably formed using an alkali metal-free alkali such as ammonia, ammonium hydrogencarbonate and ammonium carbonate.

Examples of the alkali used for the silica film-forming composition include inorganic alkalis such as ammonia, sodium hydroxide and potassium hydroxide; inorganic alkali salts such as ammonium carbonate, ammonium hydrogencarbonate, sodium carbonate and sodium hydrogencarbonate; organic alkalis such as monomethylamine, dimethylamine, trimethylamine, monoethylamine, diethylamine, triethylamine, pyridine, aniline, choline, tetramethylammonium hydroxide and guanidine; and alkali salts of organic acid, such as ammonium formate, ammonium acetate, monomethylamine formate, dimethylamine acetate, pyridine lactate guanidinoacetic acid and aniline acetate, however, the present invention is not limited thereto.

Among these, in view of the control of reaction rate, ammonia, ammonium carbonate, ammonium hydrogen carbonate, ammonium formate, ammonium acetate, sodium carbonate and sodium hydrogencarbonate are preferred. In the silica film-forming composition, the above-described alkalis may be used individually or in combination of two or more thereof.

The purity of alkali for use in the present invention is not particularly limited and an alkali widely and commonly used in industry or as a reagent may be used, but a higher purity alkali is preferred.

The effective means for increasing the silica film-forming rate is to elevate the temperature at the time of film formation. In this case, the alkali and the organic solvent used are preferably selected from those which are not easily volatilize or decompose at the film formation temperature.

In the present invention, even when the alkali for film formation is added in a trace amount, for example, in the case of sodium carbonate, on the order of 0.002 mol/liter, the film formation may be attained but the alkali may also be added in a large amount on the order of 1 mol/liter. However, if a solid alkali is added in excess of solubility, the alkali is mixed into the metal oxide powder as an impurity and this is not preferred.

By using an alkali not containing an alkali metal as a main component, the prepared particulate silica-coated metal oxide can be reduced in the alkali metal content. Among such alkalis, ammonia, ammonium carbonate and ammonium hydrogencarbonate are preferred in view of film formation rate, easiness in the removal of residual matter and the like.

In the present invention, the organic solvent used for the silica film-forming composition is preferably an organic solvent which can provide the composition as a uniform solution. Examples thereof include alcohols such as methanol, ethanol, propanol and pentanol; ether-acetals such as tetrahydrofuran and 1,4-dioxane; aldehydes such as acetaldehyde; ketones such as acetone, diacetone alcohol and methyl ethyl ketone; and polyhydric alcohol derivatives such as ethylene glycol, propylene glycol and diethylene glycol. Among these, in view of the control of reaction rate, alcohols are preferred and ethanol is more preferred. These organic solvents may be used individually or in combination of two or more thereof.

The purity of the organic solvent for use in the silica film-forming composition is not particularly limited and an organic solvent widely and commonly used in industry or as a reagent may be used, but a higher purity organic solvent is preferred.

In preparing the silica film-forming composition, a general method for preparing a solution may be used. For example, a method of adding an alkali and water each in a predetermined amount to an organic solvent, followed by stirring, and then adding tetraethoxysilane, followed by stirring, may be used. In this mixing, whichever added earlier, a coating can be formed. In mixing water and tetraethoxysilane, both are preferably diluted with an organic solvent in view of the control of reaction.

The thus-prepared silica film-forming composition is a stable composition and causes substantially no deposition or precipitation before the composition is brought into contact with metal oxide particles. When the metal oxide particles are contacted with the composition, silica starts to selectively deposit on the surface of the metal oxide particle.

The production method of titanium oxide as a starting material of the silica-coated titanium oxide is not particularly limited and any method may be used. The titanium oxide which can be used may be produced by any production method such as high-temperature vapor phase oxidation of $TiCl_4$, vapor phase hydrolysis of $TiCl_4$, sulfuric acid process and chlorine process. With respect to the crystal form of titanium oxide, any of amorphous, rutile, anatase, brookite and the like may be used and a mixture thereof may also be used. However, the titanium oxide is preferably reduced in impurities as much as possible and furthermore, in view of the control of secondary particle size, is preferably reduced in the aggregation.

The production method of zinc oxide as a starting material of the silica-coated zinc oxide is not particularly limited and any method may be used. The zinc oxide which can be used may be a zinc oxide produced by evaporation-oxidizing electrolytic zinc metal, a zinc hydroxide obtained by neutralizing an aqueous solution of water-soluble salt such as zinc sulfate or zinc chloride, or a zinc oxide obtained by calcining zinc hydroxide, zinc carbonate, zinc sulfide, zinc oxalate or the like. A mixture thereof may also be used. However, the zinc oxide is preferably reduced in impurities as much as possible and furthermore, in view of the control of secondary particle size, is preferably reduced in the aggregation.

In the present invention, titanium oxide and zinc oxide are immersed in the silica film-forming composition and kept at a predetermined temperature, whereby silica is allowed to deposit on the surfaces of titanium oxide and zinc oxide to form a silica film. With respect to the method for forming a silica film, a method of previously preparing the film-forming composition and charging titanium oxide and zinc oxide in the composition to form a silica film, a method of previously suspending titanium oxide and zinc oxide in a solvent, adding other raw material components to prepare a film-forming composition and thereby forming a silica film, or the like may be used. In other words, the order of charging raw materials of the film-forming composition, the titanium oxide and the zinc oxide is not particularly limited and whichever charged earlier, a silica film can be formed.

Among these methods, a method of preparing a suspension containing titanium oxide, zinc oxide, water, an organic solvent and an alkali and adding thereto dropwise tetraalkoxysilane diluted with an organic solvent at a constant rate is preferred, because a more dense silica film can be formed and a continuous process useful in industry can be established.

The silica film grows by the selective deposition on the surface of metal oxide and therefore, as the film formation time is longer, the coating can have a larger thickness. Of course, when the majority of silicic acid in the film-forming composition is consumed by the formation of coating, the film formation rate decreases, however, by sequentially adding silicic acid in an amount corresponding to the consumed portion, the silica film can be continuously formed at a practical film formation rate. In particular, when the silica film is formed by holding titanium oxide and zinc oxide in the film-forming composition having added thereto a silicic acid corresponding to the desired thickness of silica film for a predetermined time, thereby consuming the silicic acid, and a silicic acid corresponding to the consumed portion is further added after the silica-coated titanium oxide and silica-coated zinc oxide are taken out from the system, the composition can be continuously used in the film formation on next titanium oxide and zinc oxide and a continuous process having high profitability and good productivity can be established.

For example, in the case of a method of preparing a suspension containing titanium oxide, zinc oxide, water, an organic solvent and an alkali and adding thereto dropwise tetraalkoxysilane diluted with an organic solvent at a constant rate, a solution obtained by diluting tetra-alkoxysilane corresponding to the desired thickness of silica film with an organic solvent is added dropwise at a constant rate agreeing with the hydrolysis rate, whereby the tetraalkoxysilane is completely consumed, a dense silica film having a desired thickness can be formed and when the produced silica-coated titanium oxide and silica-coated zinc oxide are taken out from the system, a high-purity product free of residual unreacted tetraalkoxysilane can be obtained. Of course, the solvent after the silica-coated titanium oxide and the silica-coated zinc oxide are taken out can be recycled in the next film formation and a process with high profitability and high productivity can be established.

The temperature at the formation of silica film is not particularly limited but is preferably from 10 to 100° C., more preferably from 20 to 50° C. As the temperature is higher, the film formation rate is more increased, however, if the temperature is excessively high, the solution composition cannot be maintained constant due to volatilization of components in the composition, whereas if the temperature is too low, the film formation proceeds at a low rate and this is not practical.

The pH at the film formation may be sufficient if it is in the alkali region, in view of denseness of film. However, in the case of forming silica film on a metal oxide having a solubility which increases depending on the pH, the pH of the film-forming composition is preferably controlled by adjusting the amount of alkali added. In this case, with the change in the amount of alkali added, the hydrolysis rate of, for example, tetraalkoxysilane changes and therefore, the film formation temperature or the water content in the film-forming composition must be adjusted to give an appropriate hydrolysis rate.

After the film formation, the silica-coated titanium oxide or silica-coated zinc oxide can be isolated by solid-liquid separation. The isolation may be performed by a general separation method such as filtration, centrifugal sedimentation and centrifugal separation.

By performing drying after the solid-liquid separation, the obtained silica-coated titanium oxide and silica-coated zinc oxide can be reduced in the water content. In the drying, a general drying method may be used, such as natural drying, hot air drying, vacuum drying and spray drying. In the case where aggregation of particles occurs by the drying, the aggregate may be ground.

The silica film of the silica-coated titanium oxide and silica-coated zinc oxide according to the present invention has a very high shape-following capability and since primary particles of titanium oxide and zinc oxide as a substrate all are coated with a dense silica film having high covering power, the silica film is not broken by the grinding. Accordingly, the grinding method is not particularly limited and a jet mill, a high-speed rotary mill or other grinder may be used.

In the silica-coated titanium oxide and zinc oxide particles obtained by the above-described method, the ratio I of the absorption peak intensity at 1,150 to 1,250 cm$^{-1}$ to the absorption peak intensity at 1,000 to 1,100 cm$^{-1}$ on the infrared absorption spectrum ($I=I_1/I_2$, wherein $I_1$ is an absorption peak intensity at 1,150 to 1,250 cm$^{-1}$ and $I_2$ is an absorption peak intensity at 1,000 to 1,100 cm$^{-1}$) is 0.2 or more and the refractive index is 1.435 or more. In other words, the silica coating has the same chemical bond or functional group as in a silica film obtained by a conventional sol-gel method without performing calcination and therefore, exhibits specific physical properties different in the hydrophilicity, lipophilicity or the like from a silica coating obtained through calcination, nevertheless, this silica coating is dense and practical.

The term "dense" as used in the present invention means that the silica film formed has a high density and is uniform and free of pinholes or cracks. The term "practical" as used herein means that the bonding between silica and the substrate titanium oxide or zinc oxide (—Si—O-M- bonding, wherein M is Ti or Zn) is strong enough not to cause stripping or the like of the coating and the physical properties of silica-coated titanium oxide and silica-coated zinc oxide are not readily changed.

Furthermore, this silica film has good conformability to a complicated shape of the substrate titanium oxide or zinc oxide and even if the thickness is as small as about 0.5 nm, the film exhibits good covering power and high capability of concealing the photocatalytic activity. Furthermore, since the silica film can be very reduced in the alkali metal content, the silica film is not dissolved even in an atmosphere of high temperature and high humidity and the silica-coated titanium oxide and zinc oxide particles can be prevented from changing in the physical properties.

The silica-coated titanium oxide and the silica-coated zinc oxide for use in the cosmetic composition of the present invention each has a silica film thickness of 0.1 to 100 nm, preferably from 0.3 to 50 nm, more preferably from 0.5 to 25 nm. If the thickness of silica film is less than 0.1 nm, a sufficiently high effect of concealing the photocatalytic activity cannot be obtained and the obtained cosmetic composition may disadvantageously fail in having preparation form stability, whereas if it exceeds 100 nm, the obtained cosmetic composition may not have sufficiently high ultraviolet-shielding ability and this is not preferred.

The silica-coated titanium oxide and the silica-coated zinc oxide for use in the present invention each has a primary particle size of 0.01 to 0.2 μm, preferably from 0.01 to 0.12 μm. If the primary particle size departs from this range, the obtained cosmetic composition may fail in providing a high ultraviolet-shielding effect and this is not preferred.

The term "primary particle" as used in the present invention indicates a particle defined in Kiichiro Kubo et al., *Funtai (Powder)*, pp. 56–66 (1979).

In the present invention, the silica-coated titanium oxide and the silica-coated zinc oxide each has a photocatalytic activity, measured by a tetralin auto-oxidation method, of 60 Pa/min or less, preferably 50 Pa/min or less. If the photocatalytic activity measured by the tetralin auto-oxidation method exceeds 60 Pa/min, the effect of suppressing the photocatalytic activity may not be successfully attained and the obtained cosmetic composition may disadvantageously fail in having high safety and high stability.

The silica-coated titanium oxide and the silica-coated zinc oxide for use in the present invention each preferably has a dye discoloration rate, measured by a Sunset Yellow method, of 0.1 or less, more preferably 0.05 or less. If the dye discoloration rate exceeds 0.1, the effect of suppressing the photocatalytic activity is not sufficiently high and the obtained cosmetic composition may fail in having high safety and high stability.

The silica-coated titanium oxide and the silica-coated zinc oxide for use in the present invention each preferably has an organic ultraviolet absorber decomposition rate, measured by a Parsol method, of 0.02 or less, more preferably 0.01 or less. If the organic ultraviolet absorber decomposition rate measured by the Parsol method exceeds 0.02, the effect of suppressing the photocatalytic activity is not sufficiently high and the obtained cosmetic composition may disadvantageously fail in having high safety and high stability.

The silica-coated titanium oxide and the silica-coated zinc oxide for use in the present invention each preferably has an organic ultraviolet absorber decomposition percentage, measured by an ethylhexyl p-methoxycinnamate method, of 5% or less, more preferably 3% or less. If the organic ultraviolet absorber decomposition percentage measured by the ethylhexyl p-methoxycinnamate method exceeds 5%, the effect of suppressing the photocatalytic activity is not sufficiently high and the obtained cosmetic composition may disadvantageously fail in having high safety and high stability.

In the present invention, the silica-coated titanium oxide and the silica-coated zinc oxide need not be particularly calcined but, if desired, may be calcined before use.

In the present invention, the silica-coated titanium oxide and the silica-coated zinc oxide each may be subjected to a treatment of rendering the surface hydrophobic. Particularly, in the case where the silica-coated titanium oxide and silica-coated zinc oxide are used by dispersing these in an oil at the formulation of a cosmetic material, the treatment for rendering the surface hydrophobic is preferably performed before the use. The surface may be rendered hydrophobic by coating the surface using a hydrophobizing agent which is one or more selected from the group consisting of silicone oils, alkoxysilanes, silane coupling agents, and higher fatty acid salts.

Examples of the hydrophobizing agents which can be used include higher fatty acids such as waxes, higher fatty acid glyceryls, higher fatty acids, polyvalent metal salts of higher fatty acids, and polyvalent metal salts of sulfated higher aliphatic compounds; higher alcohols and derivatives thereof; fluoroorganic compounds such as perfluorinated or partially fluorinated higher fatty acids and higher alcohols; and organosilicon compounds such as silicone oils (such as dimethylpolysiloxane, methylhydrogenpolysiloxane, and modified silicone oils), silane coupling agents, alkoxysilanes, chlorosilanes, and silazanes. Polyvalent metal salts of higher fatty acids, silicone oils, silane coupling agents, and alkoxysilanes are preferably used. In particular, alkoxysilanes and silane coupling agents are preferably used in view of their effects obtained when they are actually used. The surface treatment with an alkoxysilane may be carried out using a liquid phase process or a dry process. However, a liquid phase process is more preferably employed for the following reasons: a liquid phase process makes it possible to continuously surface-treat a silica-coated metal oxide with a hydrophobizing agent by carrying out silica coating by bringing metal oxide particles into contact with a silica film-forming composition, and then, without separating the particles out, by adding a hydrophobizing agent and adding, if necessary, an alkali, water, and an organic solvent; therefore, a liquid phase process is an industrially advantageous process because intermediate steps of separating and refining the particles can be omitted.

The amount of the hydrophobizing agent to be coated may be any amount greater than or equal to the minimum coating amount sufficient to completely cover the surfaces of the silica-coated metal oxide particles, which are the raw material. The upper limit of the amount of the hydrophobizing agent used is generally not determined. However, an excessive amount is uneconomical since the amount of hydrophobizing agent precipitating in areas other than the surfaces of the metal oxide particles increases. The amount of the hydrophobizing agent to be coated is from 0.5 to 30% by mass, preferably from 0.5 to 20% by mass, more preferably from 0.8 to 10% by mass, based normally on the amount of the silica-coated metal oxide particles. If the amount of the hydrophobizing agent to coat is less than 0.5% by mass, low hydrophobicity results, whereas if it exceeds 30% by mass, the capability of ultraviolet protection may decrease in some cases.

The cosmetic composition of the present invention, which contains the above-described silica-coated titanium oxide and silica-coated zinc oxide, can be produced by a normal production method using general starting materials which can be blended in a cosmetic composition, to have an arbitrary preparation form such as W/O or O/W emulsion, liquid, solid and jell.

The cosmetic composition of the present invention is composed of a powder portion and an oil portion. The material constituting the powder portion includes, in addition to the silica-coated titanium oxide and silica-coated zinc oxide, an extender pigment (e.g., mica, talc, kaolin, calcium carbonate, magnesium carbonate, silicic acid anhydride, aluminum oxide, barium sulfate), a white pigment (e.g., titanium dioxide, zinc oxide) and a color pigment (e.g., red oxide of iron, yellow oxide of iron, black oxide of iron, chromium oxide, ultramarine, iron blue, carbon black) . These materials may be appropriately blended. In order to further improve the feeling on use, a spherical powder (e.g., nylon powder, polymethyl methacrylate powder) may also be used.

Furthermore, similarly to the silica-coated titanium oxide and silica-coated zinc oxide, fine particulate cerium oxide and the like may be used for protecting ultraviolet rays, and this particle is also preferably coated with the dense silica film of the present invention.

The oil portion blended in the cosmetic composition of the present invention includes liquid petrolatum, squalane, castor oil, glyceryl diisostearate, glyceryl triisostearate, glyceryl tri-2-ethylhexanoate, isopropyl myristate, glyceryl triisostearate, dimethylpolysiloxane, methylphenyl polysiloxane, petrolatum, diisostearyl maleate, purified lanolin and the like, however, the present invention is not limited thereto.

In the oil portion, an organic ultraviolet absorber may also be blended. The organic ultraviolet absorber means an organic compound having a function of absorbing an ultraviolet ray, consuming the energy for the generation of heat, oscillation, fluorescence, radical or the like, and thereby protecting skin.

The ultraviolet absorber which can be used in the cosmetic composition of the present invention is not particularly limited but examples thereof include ultraviolet absorbers of benzophenone type, salicylic acid type, PABA type, cinnamic acid type, dibenzoylmethane type and urocanic acid type. Specific examples thereof include 2-hydroxy-4-methoxybenzophenone, 2-hydroxy-4-methoxybenzophenone-5-sulfonic acid, sodium 2-hydroxy-4-methoxybenzophenone-5-sulfonate, dihydroxydimethoxybenzophenone, sodium dihydroxydimethoxybenzophenone-sulfonate, tetrahydroxybenzophenone, p-aminobenzoic acid, ethyl p-aminobenzoate, glyceryl p-aminobenzoate, amyl p-dimethylaminobenzoate, octyl p-dimethylaminobenzoate, ethyl p-methoxycinnamate, isopropyl p-methoxycinnamate, octyl p-methoxycinnamate, 2-ethylhexyl p-methoxycinnamate, sodium p-methoxycinnamate, glyceryl di-p-methoxycinnamate mono-2-ethylhexanoate, octyl salicylate, phenyl salicylate, homomenthyl salicylate, dipropyleneglycol salicylate, ethyleneglycol salicylate, myristyl salicylate, methyl salicylate, urocanic acid, ethyl urocanate, 4-t-butyl-4'-methoxydibenzoylmethane, 2-(2'-hydroxy-5'-methylphenyl)benzotriazole, and methyl anthranylate.

Among these, in view of ultraviolet protection and skin irritation, 2-ethylhexyl p-methoxycinnamate and 4-tert-butyl-4'-methoxydibenzoylmethane are preferred,- and 2-ethylhexyl p-methoxycinnamate is more preferable.

The amount of the ultraviolet absorber blended is from 0.1 to 10% by mass based on the entire amount of the cosmetic composition, however, an appropriate amount is preferably determined according to the ultraviolet ray-absorbing power of the absorber. In the present invention, in view of ultraviolet protection, 2-ethylhexyl p-methoxycinnamate is blended in an amount of 2 to 8% by mass, preferably from 2 to 7% by mass, more preferably from 3 to 6% by mass, and 4-tert-butyl-4'-methoxydibenzoylmethane is blended in an amount of 0.1 to 3% by mass, preferably from 0.3 to 3% by mass, more preferably from 0.5 to 2% by mass.

The silica-coated titanium oxide and silica-coated zinc oxide used in the present invention each provides a high effect of suppressing the photocatalytic activity and therefore, even when these metal oxides are used in combination with the organic ultraviolet absorber, the absorber can be prevented from decomposing, so that the obtained cosmetic composition can have high ultraviolet-shielding effect and moreover, can maintain the effect for a long period of time.

The cosmetic composition of the present invention may further contain an existing emulsifier in a general concentration. Examples of the emulsifier include those described in *Japanese Standards of Cosmetic Ingredients (JSCI), 2nd Edition, Annotation*, compiled by Nippon Koteisho Kyokai, issued by Yakuji Nippo, Ltd. (1984), *Specifications of Ingredient Other Than Those Listed in JSCI*, supervised by Examination Division, Pharmaceutical Affairs Bureau, Ministry of Health and Welfare, issued by Yakuji Nippo, Ltd. (1993), *Specifications of Ingredient Other Than Those Listed in JSCI, Supplement*, supervised by Examination Division, Pharmaceutical Affairs Bureau, Ministry of Health and Welfare, issued by Yakuji Nippo, Ltd. (1993), *The Comprehensive Licensing Standards of Cosmetics by Category*, supervised by Examination Division, Pharmaceutical Affairs Bureau, Ministry of Health and Welfare, issued by Yakuji Nippo, Ltd. (1993), and *Kesho-hin Genryo Jiten (Handbook of Cosmetic Ingredients)*, Nikko Chemicals (1991). All emulsifies described in these publications can be used. In addition, tocopheryl phosphates may also be used as the emulsifier.

In the cosmetic composition of the present invention, an existing antiinflammatory or antiphlogistic ingredient may be used in combination or may be mixed, so as to help the protection against inflammation by ultraviolet rays. The antiphlogistic ingredient which can be added to the cosmetic composition of the present invention is not particularly limited but examples thereof include aniline derivative-type antiphlogistic, salicylic acid derivative-type antiphlogistic, pyrazolone derivative-type antiphlogistic, indomethacin-type antiphlogistic, mefenamic acid-type antiphlogistic and antiinflammatory enzymatic agent, however, the present invention is not limited thereto.

When an antioxidant as a substance having an oxidation-inhibiting activity is used in combination in the cosmetic composition of the present invention, the amount of free radicals generated by ultraviolet rays can be reduced and thereby the silica-coated titanium oxide and the silica-coated zinc oxide can be more suppressed in their photocatalytic activity, as a result, a safe cosmetic composition having a remarkably excellent preparation form stability and a low phototoxicity can be obtained.

The antioxidant having an effect of suppressing the photocatalytic activity, which can be used in the cosmetic composition of the present invention, is not particularly limited but examples thereof include vitamin A, β-carotene, astaxanthin, vitamin B, vitamin C, magnesium L-ascorbic acid-2-phosphate, sodium L-ascorbic acid-2-phosphate, magnesium sodium L-ascorbic acid-2-phosphate, L-ascorbic acid-2-glucoside, L-ascorbic acid-2-phosphoric acid-5,6-benzylidene, natural vitamin E, dl-α-tocopherol, dl-α-tocopheryl acetate, sodium dl-α-tocopheryl phosphate, ubiquinone, derivatives of these vitamins, cysteine, glutathione, glutathione peroxidase, SOD, catalase, citric acid, phosphoric acid, polyphenol, catechine, tea extract, kojic acid, nucleic acid, hydroquinone and arbutin. One or more selected from these antioxidants may be blended.

Other than the above-described ingredients, the cosmetic composition of the present invention may contain ingredients commonly blended in cosmetic compositions, such as fats and oils, waxes, hydrocarbons, fatty acids, alcohols, polyhydric alcohols, saccharides, esters, metal soaps, water-soluble polymer compounds, surfactants, antioxidants, microbicide antiseptics, vitamins, hormones and coloring materials.

The silica-coated titanium oxide and the silica-coated zinc oxide are preferably blended together in the cosmetic composition of the present invention in total amount of 5 to 25% by mass, more preferably from 5 to 20% by mass, based on the total amount of the cosmetic composition. If the amount blended is less than 5% by mass, the effect of protecting ultraviolet rays is not sufficiently high, whereas if the silica-coated titanium oxide and the silica-coated zinc oxide each is blended in an amount in excess of 25% by mass, the feeling on use is disadvantageously poor because unpleasant whitening occurs at the time of application to skin or the skin is roughened.

The titanium oxide used for the purpose of protecting ultraviolet rays is generally higher in the proportion of rutile form than that of anatase form. However, the silica-coated titanium oxide for use in the present invention is greatly reduced in free radicals generated by ultraviolet rays and therefore, is not bound to the crystal form. According to the present invention, a safe cosmetic composition having excellent preparation form stability and low phototoxicity can be obtained.

The cosmetic composition of the present invention not only has preparation form stability and ultraviolet-shielding ability but also even when the particulate titanium oxide and the particulate zinc oxide each is blended in a high concentration, ensures excellent feeling on use without causing any creaky feeling or poor extension. The cosmetic composition of the present invention also has high transparency and does not cause pale finish on makeup as encountered in the case of containing a conventional particulate titanium oxide or particulate zinc oxide. Furthermore, the photocatalytic activity of titanium oxide and zinc oxide is sufficiently concealed and therefore, extremely high storage stability can be obtained without accelerating denaturation of other ingredients in the composition.

The cosmetic composition of the present invention may further contain an organic ultraviolet absorber, whereby higher ultraviolet-shielding effect and higher preparation form stability can be achieved. Furthermore, by containing an antioxidant having an oxidation-inhibiting activity, generation of active oxygen and the like can be greatly reduced and therefore, the cosmetic composition of the present invention ensures high safety to human body.

In the present invention, the thickness and the refractive index of silica film can be measured by using a silica film formed on a silicon wafer immersed in a system undergoing the synthesis of silica-coated titanium oxide and silica-coated zinc oxide. On this silicon wafer, the same silica film as on the particulate metal oxide is formed. The refractive index of silica film can be determined by an ellipsometer (LASSER ELLIPSOMETER ESM-1A, manufactured by ULVAC). The thickness can be determined using a step gauge.

The transmission infrared absorption spectrum (FT-IR-8000 manufactured by Nippon Bunko K. K.) of silica film of the silica-coated titanium oxide or silica-coated zinc oxide can be determined by a KBr method. The primary particle size of the silica-coated titanium oxide and the silica-coated zinc oxide and the thickness of silica film thereof can be determined from an image by a transmission type electron microscope.

The photocatalytic activity, namely, the initial oxygen consumption rate of the silica-coated titanium oxide and the silica-coated zinc oxide for use in the present invention can be measured by a tetralin auto-oxidation method (see, Manabu Kiyono, *Sanka Titan—Bussei to Oyo Gijutsu (Titanium Oxide— Physical Properties and Applied Technique)*, pp. 196–197, Gihodo (1991)). The measurement conditions are such that the temperature is 40° C., tetralin is 20 ml and titanium oxide is 0.02 g.

The photocatalytic activity of the silica-coated titanium oxide and the silica-coated zinc oxide for use in the present invention is further determined by a Sunset Yellow method (as a dye discoloration rate), by a Parsol 1789 method or by an ethylhexyl p-methoxycinnamate method, which are described in the present specification.

The light transmittance of the silica-coated titanium oxide and the silica-coated zinc oxide for use in the present invention is determined by a Cosmol method described in the present specification.

The cosmetic composition of the present invention provides excellent ultraviolet protection against both UVB and UVA, causes neither unpleasant whitening to the applied skin nor skin irritation and ensures good feeling on use and therefore, is suitably used as a cosmetic composition having high safety and high stability without causing decomposition of ingredients blended in the cosmetic material, such as organic ultraviolet absorber. The cosmetic composition of the present invention is particularly useful as an ultraviolet-protecting cosmetic material such as W/O or O/W milky lotion, cream, foundation and jell.

Although the above is an explanation of the case where a silica coated titanium oxide and a silica coated zinc oxide are used, use of a titanium oxide and a zinc oxide in any of the above (ii) to (ix) also exert effects similar to the effects of the use of the silica-coated titanium oxide and the silica-coated zinc oxide.

EXAMPLES

The present invention is described in greater detail below by referring to the Examples.

However, the present invention is by no means limited to these Examples.

Production Example 1
Production 1 of Silica-Coated Titanium Oxide:

In a 5 L-volume reactor, 400 mL of deionized water, 1,400 mL of ethanol (produced by Junsei Kagaku K. K.) and 75 mL of a 25 mass % aqueous ammonia (produced by Taisei Kako) were mixed and thereinto, 105 g of titanium oxide (High-Purity Titanium Oxide F-1, produced by Showa Titanium Co., Ltd.; primary particle size: 90 nm) was dispersed to prepare Suspension 1. Separately, 193 mL of tetraethoxysilane (produced by Nakarai Tesc), 36 mL of water and 144 mL of ethanol were mixed to prepare Solution 1.

To Suspension 1 under stirring with a magnetic stirrer, Solution 1 was added at a constant rate over 6 hours. The resulting solution was ripened for 12 hours. The film formation and ripening were performed at 25° C. Thereafter, the solid contents were separated by centrifugal filtration, vacuum dried at 50° C. for 12 hours and then hot-air dried at 80° C. for 12 hours to obtain silica-coated titanium oxide.

Production Example 2
Production 2 of Silica-Coated Titanium Oxide:

A silica-coated titanium oxide was obtained in the same manner as in Production Example 1 except for using titanium oxide having a different primary particle size (High-Purity Titanium Oxide F-4 produced by Showa Titanium Co., Ltd.; primary particle size: 30 nm) in place of the titanium oxide of Production Example 1.

Production Example 3
Production 3 of Silica-Coated Titanium Oxide:

In a 5 L-volume reactor, 420 mL of deionized water, 1,930 mL of ethanol (produced by Junsei Kagaku K. K.) and 75 mL of a 25 mass % aqueous ammonia (produced by Taisei Kako) were mixed and thereinto, 105 g of titanium oxide (High-Purity Titanium Oxide F-4, produced by Showa Titanium Co., Ltd.; primary particle size: 30 nm) was dispersed to prepare Suspension 2. Separately, 44 mL of tetraethoxysilane (produced by Nakarai Tesc) and 135 mL of ethanol were mixed to prepare Solution 2.

To Suspension 2 under stirring with a magnetic stirrer, Solution 2 was added at a constant rate over 6 hours. The resulting solution was ripened for 12 hours. The film formation and ripening were performed at 25° C. Thereafter, the solid-liquid separation and drying were performed in the same manner as in Production Example 1 and the obtained product was ground in a jet mill to obtain silica-coated titanium oxide.

Production Example 4
Production 1 of Silica-Coated Zinc Oxide:

In a 50 L-volume reactor, 18.25 L of deionized water, 22.8 L of ethanol (produced by Junsei Kagaku K. K.) and 124 mL of a 25 mass % aqueous ammonia (produced by Taisei Kako) were mixed and thereinto, 1.74 Kg of zinc oxide (High-Purity Zinc Oxide UFZ-40, produced by Showa Titanium Co., Ltd.; primary particle size: 27 nm) was dispersed to prepare Suspension 3. Separately, 1.62 L of tetraethoxysilane (produced by GE Toshiba Silicone) and 1.26 L of ethanol were mixed to prepare Solution 3.

To Suspension 3 under stirring, Solution 3 was added at a constant rate over 9 hours. The resulting solution was ripened for 12 hours. The film formation and ripening were performed at 45° C. Thereafter, the solid-liquid separation and drying were performed in the same manner as in Production Example 1 and the obtained product was ground in a jet mill to obtain silica-coated zinc oxide.

The silica-coated titanium oxides and silica-coated zinc oxides obtained in Production Examples 1 to 4 were determined on the transmission infrared absorption spectrum by a KBr method. As a result, with any particulate metal oxide, an absorption originated from the Si—O—Si stretching vibration was observed at 1,000 to 1,200 $cm^{-1}$, and an absorption originated from the C—H stretching vibration was not observed at 2,800 to 3,000 $cm^{-1}$, whereby the formed film was identified as silica.

Furthermore, the primary particle size, the thickness of silica film, the ratio I between absorption peak intensities on the infrared absorption spectrum, the refractive index of silica film, and the photocatalytic activity by a tetralin auto-oxidation method were measured. The results obtained are shown together in Table 1 below.

TABLE 1

|  | Primary Particle Size, nm | Film Thickness, nm | I Value | Refractive Index | Photo-catalytic Activity, Pa/min |
|---|---|---|---|---|---|
| Production Example 1 | 90 | 10 | 0.5 | 1.445 | 38 |
| Production Example 2 | 30 | 4 | 0.5 | 1.445 | 49 |
| Production Example 3 | 30 | 1 | 0.4 | 1.440 | 49 |
| Production Example 4 | 27 | 3 | 0.45 | 1.443 | 39 |

<Measurement of Light Transmittance, Cosmol Method>

The silica-coated titanium oxides of Production Examples 2 and 3, the silica-coated zinc oxide of Production Example 4, two kinds of commercially available conventional surface-treated titanium oxides (MT500SA produced by Teica Corp. and TTO-S1 produced by Ishihara Sangyo Kaisha, Ltd.) and a commercially available conventional zinc oxide (ZNO350 produced by Sumitomo Osaka Cement Corp.) were used as test substances and measured on the light transmittance by a Cosmol method. More specifically, each test substance was dispersed in polyglyceryl triisostearate (Cosmol 43) to prepare a slurry having a concentration of 1%, the slurry was placed in a 0.1 mm-thick quartz cell, and the light transmittance was measured by a spectrophotometer (UV-160, manufactured by Shimadzu Corporation). The results are shown together in FIG. 1.

Figure 1:
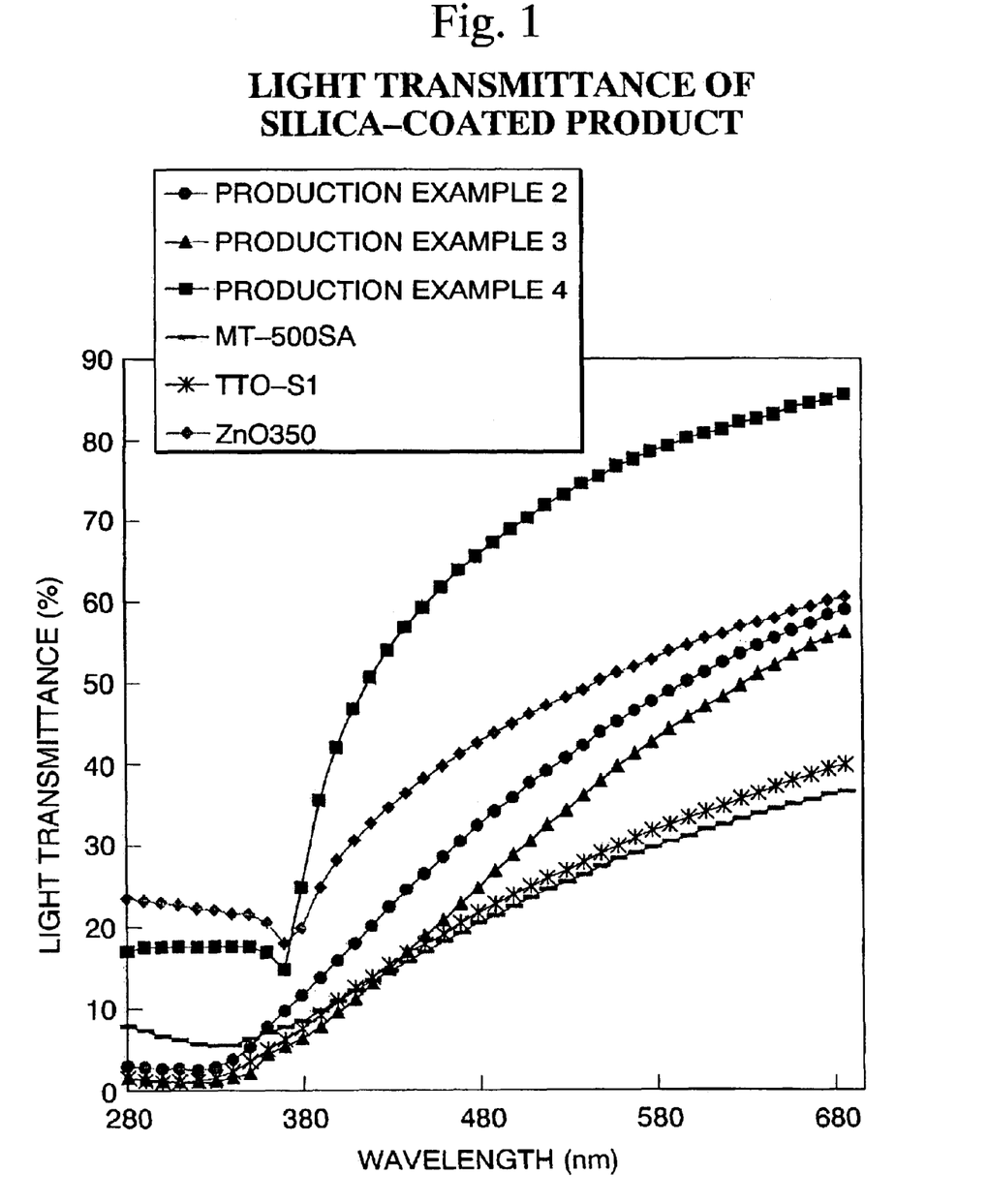
FIG. 1 is a scatter diagram showing light transmittance of silica-coated titanium oxide and silica-coated zinc oxide determined by a Cosmol method (concentration: 1% by mass, cell: 0.1 mm).

It is seen that the silica-coated titanium oxide and the silica-coated zinc oxide for use in the present invention have high light-shielding ability in the ultraviolet region and high light transmittance in the visible region as compared with the conventional products.

Example 1

Measurement of Dye Discoloration Rate, Sunset Yellow Method:

The silica-coated titanium oxides obtained in Production Examples 1 to 3, two kinds of respectively corresponding uncoated titanium oxides, two kinds of commercially available conventional surface-treated titanium oxides (MT500SA produced by Teica Corp. and TTO-S1 produced by Ishihara Sangyo Kaisha, Ltd.), the silica-coated zinc oxide obtained in Production Example 4 and an uncoated zinc oxide corresponding thereto were used as test substances and measured on the dye discoloration rate by a Sunset Yellow method.

First, Sunset Yellow FCF (produced by Wako Pure Chemical Industries, Ltd.) as a dye for cosmetics was dissolved in a 98 mass % glycerin to have a dye concentration of 0.02 mass %. Each test substance was dispersed therein to a concentration of 0.067 mass % and the resulting dispersion solution was irradiated with ultraviolet rays (ultraviolet ray intensity: 1.65 mW/cm$^2$) The absorbance at 490 nm which is a maximum absorption wavelength of Sunset Yellow FCF was measured to a light pass length of 1 mm by a spectrophotometer (UV-160, manufactured by Shimadzu Corporation) with the passage of time and the difference ($\Delta ABS_{490}$/hr) between the absorbance decrease rate here and the absorbance decrease rate in a null test (no addition of titanium oxide and zinc oxide) was calculated. The results are shown in Table 2.

TABLE 2

|  | Dye discoloration Rate ($\Delta ABS_{490}$/hr) |
|---|---|
| Production Example 1 | 0.05 |
| Production Example 2 | 0.02 |
| Production Example 3 | 0.10 |
| Production Example 4 | 0.00 |
| Conventional Surface-Treated Titanium Oxide (MT500SA) | 0.12 |
| Conventional Surface-Treated Titanium Oxide (TTO-S1) | 4.19 |
| Uncoated Titanium Oxide (starting material of Production Example 1) | 14.30 |
| Uncoated Titanium Oxide (starting material of Production Example 2) | 22.88 |
| Uncoated Zinc Oxide (starting material of Production Example 4) | 8.86 |

The silica-coated titanium oxide and the silica-coated zinc oxide for use in the present invention had a dye discoloration rate of 0.1 ($\Delta ABS_{490}$/hr) or less in any test substance and this reveals suppression in the decomposition of dye as compared with uncoated products and conventional surface-treated products.

Example 2

Measurement of Decomposition Rate of Organic Ultraviolet Absorber, Parsol 1789 Method:

The silica-coated titanium oxides obtained in Production Examples 1 to 3, two kinds of respectively corresponding uncoated titanium oxides, two kinds of conventional surface-treated particulate titanias (MT500SA produced by Teica Corp. and TTO-S1 produced by Ishihara Sangyo Kaisha, Ltd.), the silica-coated zinc oxide obtained in Production Example 4 and an uncoated zinc oxide were used as test substances and measured on the organic ultraviolet absorber decomposition rate by a Parsol method.

More specifically, each test substance was dispersed in a polyethylene glycol 300 solution of 4-tert-butyl-4'-methoxydibenzoylmethane (Parsol 1789) (0.045% by mass as a Parsol 1789 concentration) to form a 1 wt % slurry. Then, 1.2 g of the slurry was charged in a glass container, ultraviolet rays (1.65 mW/cm$^2$) were irradiated for 10 hours, 1 g was then sampled and thereto, 2 mL of isopropyl alcohol, 2 mL of hexane and 3 mL of distilled water were sequentially added. The mixture was stirred, Parsol 1789 was extracted in the hexane phase, and the absorbance (at 340 nm) of the hexane phase was measured to a light pass length of 1 mm by a spectrophotometer (UV-160, manufactured by Shimadzu Corporation). The difference ($\Delta ABS_{340}$/hr) between the absorbance decrease rate at 340 nm and the absorbance decrease rate in a null test (no addition of titanium oxide and zinc oxide) was calculated.

The results obtained are shown together in Table 3.

TABLE 3

|  | Decomposition Rate ($\Delta ABS_{340}$/hr) |
|---|---|
| Production Example 1 | 0.001 |
| Production Example 2 | 0.001 |
| Production Example 3 | 0.017 |
| Production Example 4 | 0.002 |
| Conventional Surface-Treated Titanium Oxide (MT500SA) | 0.024 |
| Conventional Surface-Treated Titanium Oxide (TTO-S1) | 0.044 |
| Uncoated Titanium Oxide (starting material of Production Example 1) | 0.120 |

TABLE 3-continued

| | Decomposition Rate ($\Delta ABS_{340}/hr$) |
|---|---|
| Uncoated Titanium Oxide (starting material of Production Example 2) | 0.175 |
| Uncoated Zinc Oxide (starting material of Production Example 4) | 0.066 |

The silica-coated titanium oxide and silica-coated zinc oxide which can be used in the present invention had a decomposition rate of 0.02 ($\Delta ABS_{340}/hr$) or less in any test substance and this reveals that the ultraviolet absorber decomposability was extremely low as compared with uncoated products and conventional surface-treated products.

Example 3
Measurement of Decomposition Rate of Organic Ultraviolet Absorber, Ethylhexyl p-Methoxycinnamate Method:

The silica-coated titanium oxides obtained in Production Examples 1 to 3, two kinds of respectively corresponding uncoated titanium oxides, two kinds of conventional surface-treated particulate titanias (MT-100T produced by Teica Corp. and TTO-S1 produced by Ishihara Sangyo Kaisha, Ltd.), the silica-coated zinc oxide obtained in Production Example 4 and an uncoated zinc oxide were used as test substances and measured on the organic ultraviolet absorber decomposition percentage by an ethylhexyl p-methoxycinnamate method.

More specifically, each test substance was dispersed in a polyethylene glycol 300 solution of 2-ethylhexyl p-methoxycinnamate (0.05% by mass as a 2-ethylhexyl p-methoxycinnamate concentration) to form a 0.33 wt % slurry. Then, 1.2 g of the slurry was charged in a glass container, ultraviolet rays (1.65 mW/cm$^2$) were irradiated for 90 minutes, 1 g was then sampled and thereto, 2 mL of isopropyl alcohol, 2 mL of hexane and 3 mL of distilled water were sequentially added. The mixture was stirred, 2-ethylhexyl p-methoxycinnamate was extracted in the hexane phase, and the absorbance (at 300 nm) of the hexane phase was measured to a light pass length of 1 mm by a spectrophotometer (UV-160, manufactured by Shimadzu Corporation). From the difference between the absorbance decrease rate at 300 nm and the absorbance decrease rate in a null test (no addition of titanium oxide and zinc oxide), the decomposition percentage of 2-ethylhexyl p-methoxycinnamate was calculated. The results are shown in Table 4 below.

TABLE 4

| | Decomposition Rate % |
|---|---|
| Production Example 1 | 0.5 |
| Production Example 2 | 0.5 |
| Production Example 3 | 2.0 |
| Production Example 4 | 0.5 |
| Conventional Surface-Treated Titanium Oxide (MT-100T) | 16.0 |
| Conventional Surface-Treated Titanium Oxide (TTO-S1) | 9.0 |
| Uncoated Titanium Oxide (starting material of Production Example 2) | 80.0 |
| Uncoated Zinc Oxide (starting material of Production Example 4) | 21.0 |

The silica-coated titanium oxide and the silica-coated zinc oxide which can be used in the present invention had a decomposition percentage of 5% or less in any substance, revealing that the ultraviolet absorber decomposability was extremely low as compared with uncoated products and conventional surface-treated products.

Example 4
Measurement of Powder Kinetic Friction Coefficient, Glass Plate Method:

The silica-coated titanium oxides obtained in Production Examples 1 to 3, two kinds of respectively corresponding uncoated titanium oxides, two kinds of conventional surface-treated titanium oxides (MT500SA produced by Teica Corp. and TTO-S1 produced by Ishihara Sangyo Kaisha, Ltd.), the silica-coated zinc oxide obtained in Production Example 4 and an uncoated zinc oxide were used as test substances and measured on the powder kinetic friction coefficient by a glass plate method. More specifically, each test substance powder was dispersed on a glass plate of 100×200 mm to an amount of 10 mg/cm$^2$. This glass plate was placed on the test table of a surface property measuring apparatus (HEIDON-14DR manufactured by Shinto Kagaku K. K.) and the coefficient of kinetic friction was measured under conditions such that the load was 22.2 g/cm$^2$, the moving speed was 200 mm/min and the moving distance was 20 mm. The results are shown in Table 5.

TABLE 5

| | Coefficient of Powder Kinetic Friction |
|---|---|
| Production Example 1 | 0.441 |
| Production Example 2 | 0.447 |
| Production Example 3 | 0.510 |
| Production Example 4 | 0.490 |
| Conventional Surface-Treated Titanium Oxide (MT500SA) | 0.554 |
| Conventional Surface-Treated Titanium Oxide (TTO-S1) | 0.685 |
| Uncoated Titanium Oxide (starting material of Production Example 1) | 0.584 |
| Uncoated Titanium Oxide (starting material of Production Example 2) | 0.641 |
| Uncoated Zinc Oxide (starting material of Production Example 4) | 0.640 |

The silica-coated titanium oxide and the silica-coated zinc oxide for use in the present invention had a coefficient of kinetic friction of 0.550 or less in any test substance, whereas uncoated products and conventional surface-treated products exhibited a value in excess of 0.550.

Examples 5 to 7

W/O Sunscreen milky lotions each having a composition shown in Table 6 (expressed by mass % based on the entire amount of the cosmetic material) were prepared by an ordinary method. In Examples 5 to 7 and Comparative Examples 1 to 3, the titanium oxide used was the silica-coated titanium oxide of Production Example 3 and the zinc oxide was the silica-coated zinc oxide of Production Example 4. However, before use, each metal oxide was subjected to a treatment for rendering the surface hydrophobic to 3% by mass of dimethylpolysiloxane so as to allow the silica-coated titanium oxide and silica-coated zinc oxide to disperse in the oil phase side of the W/O milky lotion (hereinafter, these hydrophobitized products are called a "silicone-treated silica-coated titanium oxide" or a "silicone-treated silica-coated zinc oxide"). The thus-prepared formulation products were evaluated as follows on the ultraviolet protection effect, the transparency at the application and the feeling on use after the application to skin.

<Evaluation of Ultraviolet Protection Effect>

SPF was measured under test conditions according to the standards of SPF Measuring Method (JCIA method) provided by the Japan Cosmetic Industry Association (JCIA) in 1992.

PA was measured under test conditions according to the standards of UVA Protection Effect Measuring Method provided by the Japan Cosmetic Industry Association in 1996.

<Evaluation of Transmittance at the Application: Glass Plate Coating Method>

A formulation product was coated on a glass plate to a coated thickness of 10 μm and left standing at room temperature for 1 hour. Thereafter, the whiteness degree W value was measured by a color difference meter (TC-8600, manufactured by Tokyo Denshoku) using a CIE color specification system with black paper (the black part of a hiding chart was used therefor) placed on the back.

<Evaluation of Feeling on Use after Application to Skin>

Each formulation product was applied to the inner arm part of 10 professional panelists and rated ⊚ for the evaluation of good feeling by 8 to 10 panelists, ○ by 5 to 7 panelists, Δ by 2 to 4 panelists, or × by 2 to 4 panelists. The results are shown together in Table 6.

TABLE 6

| Ingredients (mass %) | Example 5 | Example 6 | Example 7 | Comparative Example 1 | Comparative Example 2 | Comparative Example 3 |
|---|---|---|---|---|---|---|
| Squalane | 5.0 | 5.0 | 5.0 | 5.0 | 5.0 | 5.0 |
| Decamethyl-cyclopenta-siloxane | 12.0 | 12.0 | 12.0 | 12.0 | 12.0 | 12.0 |
| Decaglyceryl pentaoleate | 2.5 | 2.5 | 2.5 | 2.5 | 2.5 | 2.5 |
| Hexaglyceryl polylisinolate | 0.3 | 0.3 | 0.3 | 0.3 | 0.3 | 0.3 |
| Silicone-treated silica-coated titanium oxide | 6.0 | 3.75 | 3.75 | 15.0 | 7.5 | — |
| Silicon-treated silica-coated zinc oxide | 9.0 | 11.25 | 11.25 | — | 7.5 | 15.0 |
| 2-Ethylhexyl p-methoxy-cinnamate | 6.0 | 6.0 | 3.0 | 6.0 | 6.0 | 6.0 |
| 4-tert-Butyl-4'-methoxydi-benzoyl-methane | — | — | 2.0 | — | — | — |
| Magnesium sulfate | 0.5 | 0.5 | 0.5 | 0.5 | 0.5 | 0.5 |
| Glycerin | 5.0 | 5.0 | 5.0 | 5.0 | 5.0 | 5.0 |
| Paraben | 0.2 | 0.2 | 0.2 | 0.2 | 0.2 | 0.2 |
| Purified water | Balance | Balance | Balance | Balance | Balance | Balance |
| SPF | 41.0 | 40.3 | 41.8 | 42.0 | 41.0 | 32.0 |
| PFA | 7.8 | 7.8 | 10.0 | 7.3 | 7.3 | 5.9 |
| PA | ++ | ++ | +++ | ++ | ++ | ++ |
| W (whiteness) | 12.0 | 11.0 | 10.5 | 31.5 | 22.5 | 5.5 |
| Feeling on use | ⊚ | ⊚ | ⊚ | ⊚ | ⊚ | ⊚ |

As is apparent from the results in Table 6, when the amount of titanium oxide as expressed by the mass ratio of particulate titanium oxide to particulate zinc oxide is 2:3 or more, the W value is as high as to exceed 20 and the unpleasant whitening is serious. Also, when the amount of titanium oxide as expressed by the mass ratio of particulate titanium oxide to particulate zinc oxide is 1:5 or less, the capability of ultraviolet protection decreases despite good transparency at the time of application. On the other hand, the products of the present invention as having a specific mass ratio of particulate titanium oxide to particulate zinc oxide, exhibits good transparency with a W value of 15 or less while maintaining the same capability of ultraviolet protection as in the sole use of titanium oxide and at the same time, exhibits good use feeling. Furthermore, as is apparent from Examples 2 and 3, the products of the present invention are free of decomposition of 2-ethylhexyl p-methoxycinnamate or 4-tert-butyl-4'-methoxydibenzoylmethane and therefore, favored with high safety and high stability.

Examples 8 to 10

W/O Sunscreen milky lotions each having a composition shown in Table 7 (expressed by mass % based on the entire amount of the cosmetic material) were prepared by an ordinary method. In Examples 8 to 10 and Comparative Examples 4 to 6, the titanium oxide used was the silica-coated titanium oxide of Production Example 3 and the zinc oxide used was the silica-coated zinc oxide of Production Example 4. The formulation products prepared were evaluated on the ultraviolet protection effect, the transparency at the application and the feeling on use after the application to skin in the same manner as in Examples 5 to 7.

TABLE 7

| Ingredients (mass %) | Example 8 | Example 9 | Example 10 | Comparative Example 4 | Comparative Example 5 | Comparative Example 6 |
|---|---|---|---|---|---|---|
| Methylpoly-siloxane | 10.0 | 10.0 | 10.0 | 10.0 | 10.0 | 10.0 |
| Decamethyl-cyclopenta-siloxane | 25.0 | 25.0 | 25.0 | 25.0 | 25.0 | 25.0 |
| Polyether-modified silicone | 1.0 | 1.0 | 1.0 | 1.0 | 1.0 | 1.0 |
| Silicone-treated silica-coated titanium oxide | 6.0 | 3.75 | 3.75 | 15.0 | 7.5 | — |
| Silicone-treated silica-coated zinc oxide | 9.0 | 11.25 | 11.25 | — | 7.5 | 15.0 |
| 2-Ethylhexyl p-methoxy-cinnamate | 6.0 | 6.0 | 3.0 | 6.0 | 6.0 | 6.0 |
| 4-tert-Butyl-4'-methoxydi-benzoyl-methane | — | — | 2.0 | — | — | — |
| Glycerin | 5.0 | 5.0 | 5.0 | 5.0 | 5.0 | 5.0 |
| Purified water | Balance | Balance | Balance | Balance | Balance | Balance |
| SPF | 42.0 | 41.0 | 43.0 | 43.0 | 41.0 | 31.0 |
| PFA | 7.9 | 7.8 | 10.6 | 7.6 | 7.8 | 6.1 |
| PA | ++ | ++ | +++ | ++ | ++ | ++ |
| W (whiteness) | 11.0 | 10.0 | 9.5 | 35.0 | 20.0 | 7.0 |
| Feeling on use | ⊚ | ⊚ | ⊚ | ⊚ | ⊚ | ⊚ |

Similarly to Examples 5 to 7, when the amount of titanium oxide as expressed by the mass ratio of particulate titanium oxide to particulate zinc oxide is 2:3 or more, the W value is as high as to exceed 20 and the unpleasant whitening is serious. Also, when the amount of titanium oxide as expressed by the mass ratio of particulate titanium oxide to particulate zinc oxide is 1:5 or less, the capability of ultraviolet protection decreases despite good transparency at the time of application. On the other hand, the products of the present invention as having a specific mass ratio of particulate titanium oxide to particulate zinc oxide, exhibits good transparency with a W value of 15 or less while maintaining the same capability of ultraviolet protection as in the sole use of titanium oxide and at the same time, exhibits good use feeling. Furthermore, as is apparent from Examples 2 and 3, the products of the present invention are free of decomposition of 2-ethylhexyl p-methoxycinnamate or 4-tert-butyl-4'-methoxydibenzoylmethane and therefore, favored with high safety and high stability.

INDUSTRIAL APPLICABILITY

The cosmetic composition of the present invention has excellent ultraviolet protection against both UVB and UVA, causes neither unpleasant whitening to the applied skin nor skin irritation, and ensures good feeling on use and high safety and high stability without causing decomposition of the ingredients blended in the cosmetic material, such as organic ultraviolet absorber. Therefore, the cosmetic composition of the present invention is particularly useful for use in cosmetics having ultraviolet protection effect.

What is claimed is:

1. A cosmetic composition having blended therein silica-, alumina- or alumina/silica-coated particulate titanium oxide and silica-, alumina- or alumina/silica-coated particulate zinc oxide at a mass ratio of 1:4 to 2:3, the particulate titanium oxide having an average primary particle size of 0.01 to 0.2 $\mu$m. and the particulate zinc oxide having an average primary particle size of 0.01 to 0.033 $\mu$m.

2. The cosmetic composition as claimed in claim 1, which comprises the silica-, alumina- or alumina/silica-coated particulate titanium oxide and the silica-, alumina- or alumina/silica-coated particulate zinc oxide in total amount of 5 to 25% by mass based on the amount of the cosmetic composition.

3. The cosmetic composition as claimed in claim 1, which comprises an organic ultraviolet absorber.

4. The cosmetic composition as claimed in claim 1, which comprises from 2 to 8% by mass of 2-ethylhexyl p-methoxycinnamate.

5. The cosmetic composition as claimed in claim 1, which comprises from 0.1 to 3% by mass of 4-tert-butyl-4'-methoxydibenzoylmethane.

6. The cosmetic composition as claimed in claim 1, wherein the cosmetic composition maintains the same SPF (Sun Protection Factor) value as in the sole use of titanium oxide and when said cosmetic composition is applied to a thickness of 10 $\mu$m, the whiteness W value measured using the CIE (International Commission on Illumination) color specification system is 20 or less.

7. The cosmetic composition as claimed in claim 6, wherein the SPF (Sun Protection Factor) value is 30 or more.

8. The cosmetic composition as claimed in claim 1, where the PFA (Protection Factor of UVA) of the cosmetic composition is 4 or more.

9. The cosmetic composition as claimed in claim 6, wherein the W value is 15 or less.

10. The cosmetic composition as claimed in claim 1, wherein the particulate titanium oxide and the particulate zinc oxide each is coated with silica and the silica film has a thickness of 0.1 to 100 nm.

11. The cosmetic composition as claimed in claim 10, wherein the surfaces of the silica-coated particulate titanium oxide and zinc oxide are further made hydrophobic by using a hydrophobizing agent.

12. The cosmetic composition as claimed in claim 11, wherein the hydrophobizing agent is one or more selected from the group consisting of silicone oils, alkoxysilanes, silane coupling agents, and higher fatty acid salts.

13. The cosmetic composition as claimed in claim 10, wherein the silica-coated particulate titanium oxide and the silica-coated particulate zinc oxide each has a photocatalytic activity, determined by the tetralin auto-oxidation method, of 60 Pa/mm or less.

14. The cosmetic composition as claimed in claim 10, wherein the silica-coated particulate titanium oxide and the silica-coated particulate zinc oxide each has a dye discoloration rate ($\Delta ABS_{490}$/hr), determined by a Sunset Yellow method, of 0.1 or less.

15. The cosmetic composition as claimed in claim 10, wherein the silica-coated particulate titanium oxide and the silica-coated particulate zinc oxide each has an organic ultraviolet absorber decomposition rate ($\Delta ABS_{340}$/hr), determined by a Parsol 1789 method, of 0.02 or less.

16. The cosmetic composition as claimed in claim 10, wherein the silica-coated particulate titanium oxide and the silica-coated particulate zinc oxide each has an organic ultraviolet absorber decomposition percentage, determined by an ethylhexyl p-methoxycinnamate method, of 5% or less.

17. The cosmetic composition as claimed in claim 10, wherein the silica-coated particulate titanium oxide and the silica-coated particulate zinc oxide each has a kinetic friction coefficient, determined by a glass plate method, of 0.550 or less.

18. A method for producing a cosmetic composition, comprising bringing particulate titanium oxide and particulate zinc oxide each having an average primary particle size of 0.01 to 0.2 $\mu$m as a mixture (at a mass ratio of 1:4 to 2:3) or separately into contact with a silica film-forming composition containing water, an alkali, an organic solvent and a silic acid having neither an organic group nor a halogen or a precursor capable of producing said silic acid, with the water/organic solvent ratio being from 0.1 to 10 and the silica acid concentration being from 0.0001 to 5 mol/liter, thereby coating the particulate titanium oxide and the particulate zinc oxide with silica, and drying and blending these particles.

19. The method for producing a cosmetic composition as claimed in claim 18, which comprises blending from 2 to 8% by mass of 2-ethylhexyl p-methoxycinnamate.

20. The method for producing a cosmetic composition as claimed in claim 18, which comprises blending from 0.1 to 3% by mass of 4-tert-butyl-4'-methoxydibenzoylmethane.

21. An ultraviolet-protecting cosmetic material comprising the cosmetic composition claimed in any one of claims 1 to 17.

22. The ultraviolet-protecting cosmetic material as claimed in claim 21, which is a W/O or O/W milky lotion, a cream, a foundation or a gel.

* * * * *